United States Patent [19]

Segawa et al.

[11] Patent Number: 5,210,308

[45] Date of Patent: May 11, 1993

[54] PROCESS FOR THE PRODUCTION OF MODIFIED H-MORDENITE, CATALYST COMPRISING SAID H-MORDENITE AND PROCESS FOR THE SYNTHESIS OF METHYLAMINE WITH THE USE OF THE SAME

[75] Inventors: Kouichi Segawa; Azusa Sugiyama, both of Kanagawa; Hiroyasu Tachibana, Tokyo; Yasuhiko Kurusu, Kanagawa, all of Japan

[73] Assignee: Nitto Chemical Industry Co., Ltd., Tokyo, Japan

[21] Appl. No.: 868,844

[22] Filed: Apr. 16, 1992

Related U.S. Application Data

[62] Division of Ser. No. 596,262, Oct. 12, 1990, Pat. No. 5,137,854.

[30] Foreign Application Priority Data

Mar. 13, 1990 [JP] Japan .................................. 2-61417

[51] Int. Cl.$^5$ ............................................. C07C 209/16
[52] U.S. Cl. ...................................... 564/479; 564/463
[58] Field of Search ................................ 564/479, 463

[56] References Cited

U.S. PATENT DOCUMENTS

4,918,233  4/1990  Deeba et al. ........................ 564/479

Primary Examiner—Allen J. Robinson
Assistant Examiner—Scott C. Rand
Attorney, Agent, or Firm—Sughrue, Mion, Zinn, Macpeak & Seas

[57] ABSTRACT

A process for the production of a modified H-mordenite which comprises bringing an alkali metal or alkaline earth metal-type mordenite into contact with $SiCl_4$ under a heating condition and then converting the treated mordenite into an H-type via ion exchange, a catalyst comprising the modified H-mordenite and a process for the production of methylamines using the use of the catalyst.

2 Claims, 4 Drawing Sheets

FIG. 3A(1) 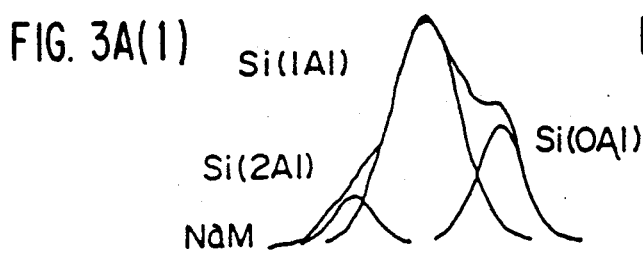
FIG. 3A(2) 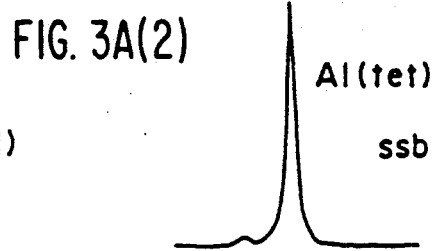
FIG. 3B(1) 
FIG. 3B(2) 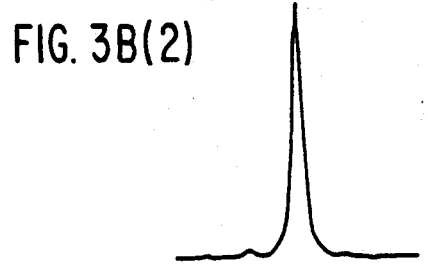
FIG. 3C(1) 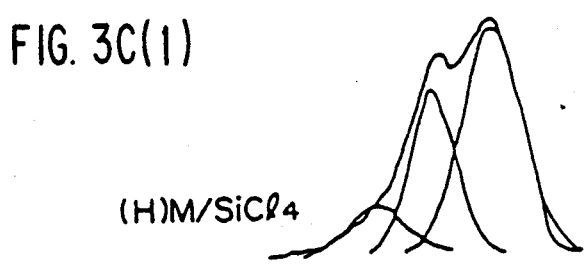
FIG. 3C(2) 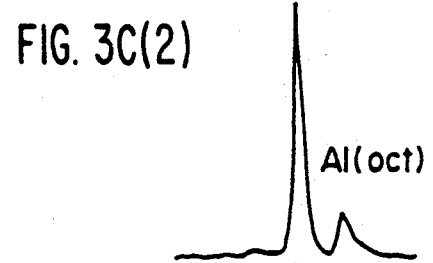
FIG. 3D(1) 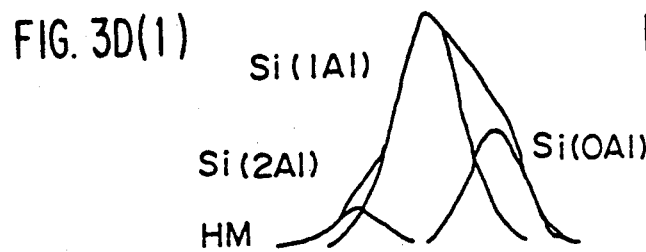
FIG. 3D(2) 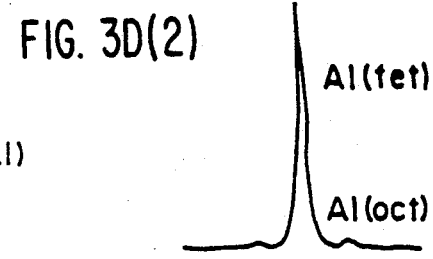
FIG. 3E(1) 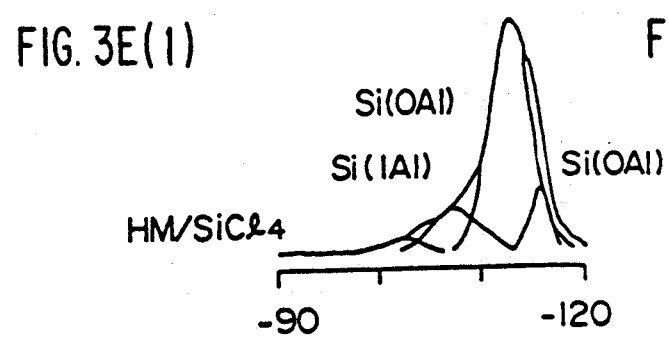
FIG. 3E(2) 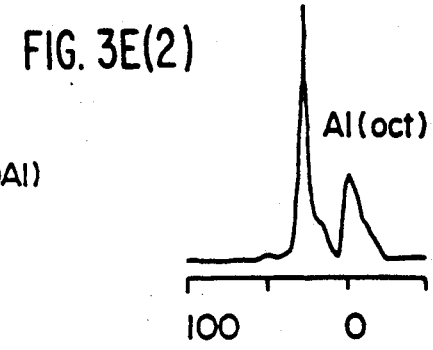
Chemical Shift         Chemical Shift

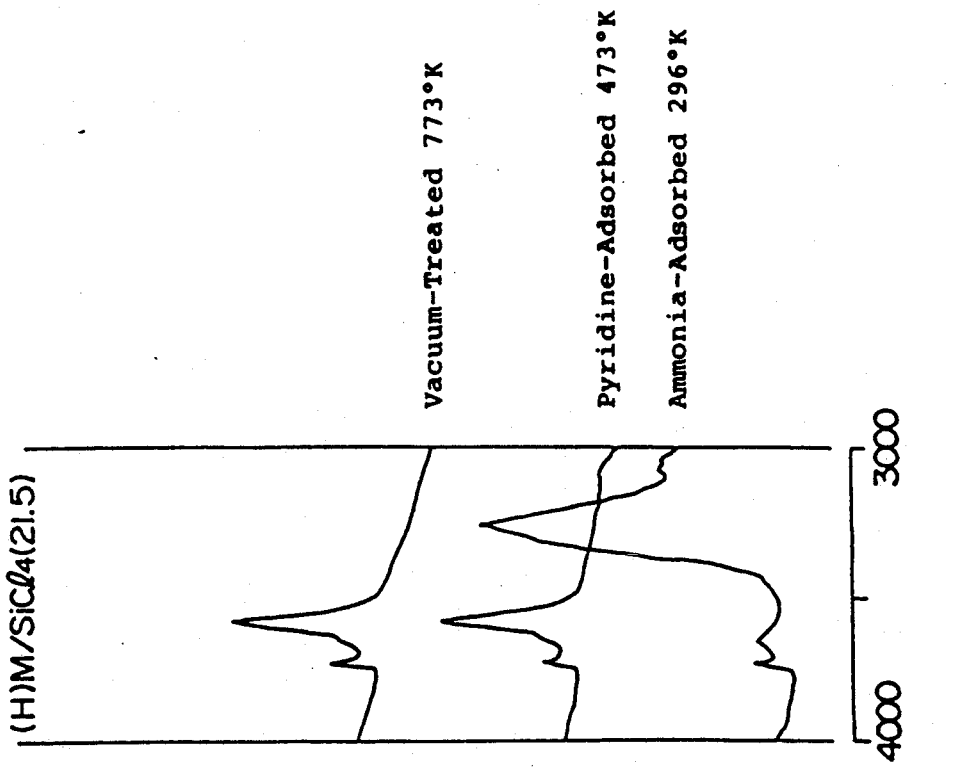

PROCESS FOR THE PRODUCTION OF MODIFIED H-MORDENITE, CATALYST COMPRISING SAID H-MORDENITE AND PROCESS FOR THE SYNTHESIS OF METHYLAMINE WITH THE USE OF THE SAME

This is a divisional of application Ser. No. 07/596,262 filed Oct. 12, 1990 now U.S. Pat. No. 5,137,854.

FIELD OF THE INVENTION

This invention relates to a process for the production of a modified H-mordenite.

Furthermore, the present invention relates to a catalyst comprising a modified H-mordenite produced by the process and a process for the synthesis of methylamines with the use of the catalyst.

BACKGROUND OF THE INVENTION

It is generally believed that the reaction of a zeolite with $SiCl_4$ results in the removal of aluminum. It is suggested that not only Y-zeolite but also H-mordenite would undergo the above-mentioned reaction in accordance with the following:

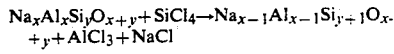

$$Na_xAl_xSi_yO_{x+y} + SiCl_4 \rightarrow Na_{x-1}Al_{x-1}Si_{y+1}O_{x+y} + AlCl_3 + NaCl$$

[see "Zeolite no Kagaku to Oyo", H. Tominaga, ed. pp. 100–102, Mar. 30, 1987 (Kodansha)].

On the other hand, it is known that the activity of a zeolite to be used as a catalyst largely depends on the amount of Al present in the crystal skeleton thereof and that the activity decreases as the amount of Al present decreases accompanied by a decrease in the number of acid sites. In this case, however, the acid strength increases. It is further known, on the other hand, that a zeolite having a pore size suitable for use as a catalyst should be selected.

In order to control the pore size of a zeolite, introduction of a cation or reaction of the hydroxyl groups of the zeolite with, for example, tetramethylsilane or tetramethoxysilane have been proposed. However, the former method results in a decrease in the amount of the solid acid, while the reactants required in the latter method are expensive organic compounds (see "Zeolite no Kagaku to Oyo", supra, p. 105).

Therefore, it has been considered that the decrease in solid acid sites caused by the introduction of a cation for the controlling of the pore size could be recovered by effecting another treatment (see "Zeolite no Kagaku to Oyo", supra, p. 105).

SUMMARY OF THE INVENTION

An object of the present invention is to develop a method for treating a zeolite whereby the pore size of the zeolite can be controlled without deteriorating the solid acid characteristics of the zeolite.

Another object of the present invention is to provide a highly active and highly selective catalyst available for a reaction involving a molecule of limited molecular size of approximately 5 Å or below, for example, the synthesis of monomethylamine or dimethylamine or the synthesis of a p-isomer of an aromatic compound such as p-xylene, since the above-mentioned zeolite, which has a controlled pore size and contains a number of solid acid site, shows a high shape-selectivity and a high catalytic activity for such reactions as described above.

Methylamines are commonly synthesized from methanol and ammonia with the use of a solid acid catalyst. This reaction depends on thermodynamic equilibrium and trimethylamine (TMA) is formed as the major product together with dimethylamine (DMA) and monomethylamine (MMA) thereby. In addition, dimethyl ether (DME) is formed as a by-product. However, dimethylamine, which is useful as an organic intermediate or a solvent, is exclusively required industrially.

Accordingly, a further object of the present invention is to provide a catalyst whereby dimethylamine and monomethylamine can be formed at high yields while only a small amount of trimethylamine is formed in the synthesis of methylamines.

As described above, it is generally believed that the reaction of a zeolite with $SiCl_4$ would result in the removal of aluminum. However, the present inventors have surprisingly found out that no aluminum is removed when an alkali metal or alkaline earth metal type mordenite is selected, thus completing the present invention.

Namely, a first embodiment of the present invention is a process for the production of a modified H-mordenite which comprises treating an alkali metal or alkaline earth metal type mordenite with $SiCl_4$ and then converting the modified mordenite into an H-type via ion exchange.

A second embodiment of the present invention provides a catalyst comprising a modified H-mordenite obtained by the above-mentioned process.

A third embodiment of the present invention provides a process for the synthesis of methylamines through the reaction between methanol and ammonia wherein the above-mentioned catalyst is employed as a catalyst.

BRIEF DESCRIPTION OF THE DRAWINGS

FIG. 3 shows the results of NMR analysis: wherein
NaM represents Na-mordenite, $NaM/SiCl_4$ represents Na-mordenite treated with $SiCl_4$, HM represents H-mordenite, $HM/SiCl_4$ represents H-mordenite treated with $SiCl_4$ and $(H)M/SiCl_4$ represents the modified H-mordenite prepared in accordance with the method of the present invention;

Figure 1:
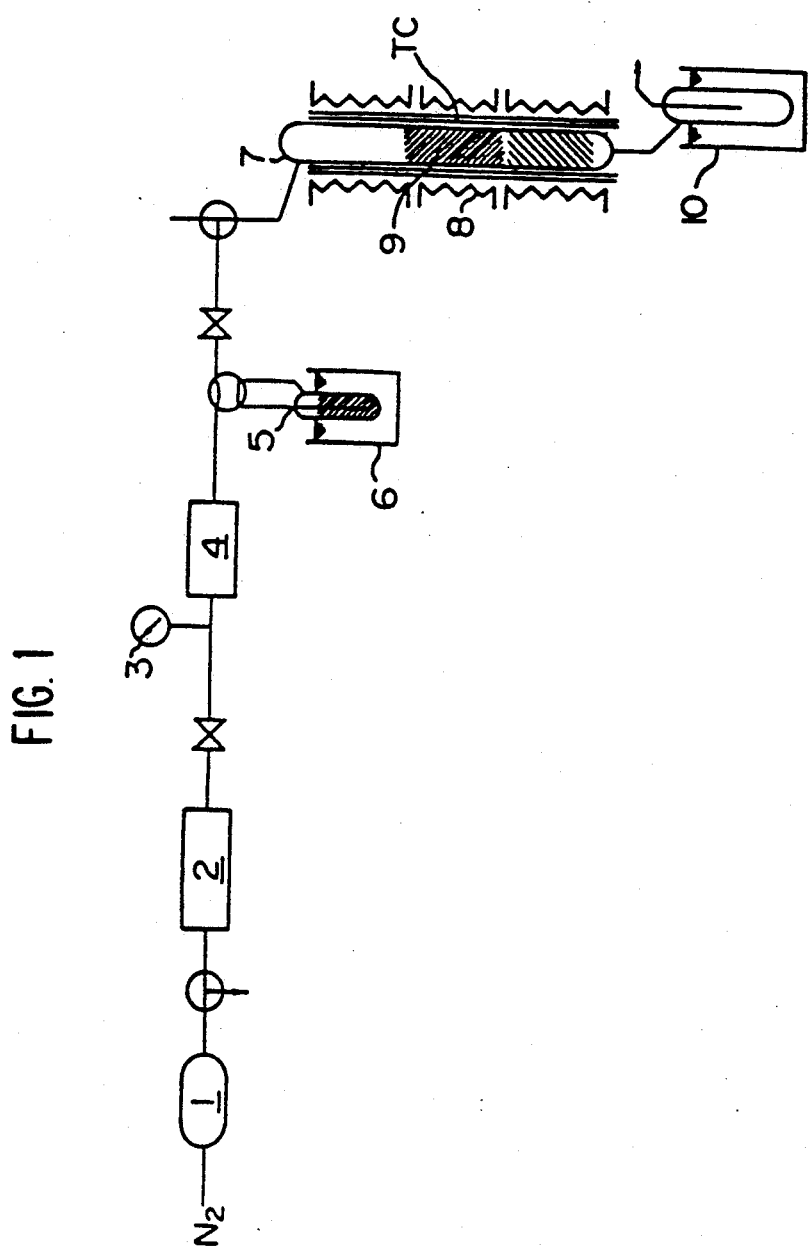
FIG. 1 shows a $SiCl_4$ atmospheric pressure flow-through type treatment device employed in the Test Examples and the Examples in the present invention.

$a_1$ shows the $^{29}Si$ nuclear magnetic resonance of NaM determined in examining the environments of the Si atom;

$a_2$ shows the $^{27}Al$ nuclear magnetic resonance of NaM determined in examining the environments of the Al atom;

$b_1$ shows the $^{29}Si$ nuclear magnetic resonance of $NaM/SiCl_4$ determined in examining the environments of the Si atom;

$b_2$ shows the $^{27}Al$ nuclear magnetic resonance of $NaM/SiCl_4$ determined in examining the environments of the Al atom;

$c_1$ shows the $^{29}Si$ nuclear magnetic resonance of $(H)M/SiCl_4$ determined in examining the environments of the Si atom;

$c_2$ shows the $^{27}Al$ nuclear magnetic resonance of $(H)M/SiCl_4$ determined in examining the environments of the Al atom;

$d_1$ shows the $^{29}Si$ nuclear magnetic resonance of HM determined in examining the environments of the Si atom;

$d_2$ shows the $^{27}Al$ nuclear magnetic resonance of HM determined in examining the environments of the Al atom;

$e_1$ shows the $^{29}Si$ nuclear magnetic resonance of HM/SiCl$_4$ determined in examining the environments of the Si atom; and $e_2$ shows the $^{27}Al$ nuclear magnetic resonance of HM/SiCl$_4$ determined in examining the environments of the Al atom.

FIG. 4 shows the results of IR analysis wherein A shows a case of HM, B shows that of HM/SiCl$_4$ and C shows that of (H)M/SiCl$_4$.

The reference numerals in the above figures have the following meanings: 1: gas dryer; 2: flow controller; 3: pressure gauge; 4: flow meter; 5: SiCl$_4$ bubbler; 6: water tank; 7: reaction tube; 8: oven; 9: catalyst layer; 10: liquid nitrogen trap; 11: gas dryer; 12: thermal mass flow controller; 13: methanol saturation device; 14: gas mixer; 15: pressure gauge; 16: flow meter; 17: reaction tube; 18: oven; 19: preheating region; and 20: sample outlet.

DETAILED DESCRIPTION OF THE INVENTION

As described above, it is highly surprising that a modified H-mordenite, which is obtained by treating a specific zeolite with SiCl$_4$ followed by ion exchange, not only has a uniformly narrowed pore structure but also provides solid acid characteristics (i.e., another important factor as a catalyst) since the removal of aluminum does not occur.

An embodiment of the present invention is described by reference to the following reaction scheme:

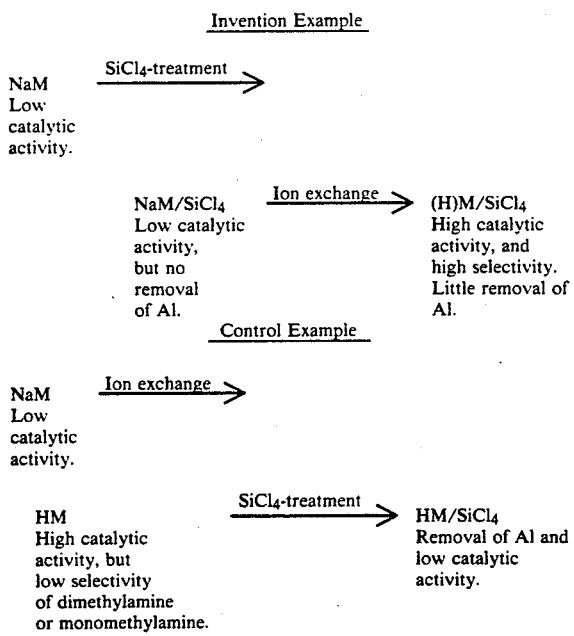

Note: M represents mordenite.

The starting material mordenite for the present invention may be of an alkali metal type such as Na-mordenite and K-mordenite or of an alkaline earth metal type such as Ca-mordenite and Mg-mordenite, preferably alkali metal type mordenite. Molecular formula of mordenite is Me$_{1/n}$(AlSi$_5$O$_{12}$)·3H$_2$O wherein Me is proton or a n-valent metal cation, and therefore alkali metal type mordenite is represented by a formula Me(AlSi$_5$O$_{12}$)·3H$_2$O wherein Me is an alkali metal cation.

In the present invention, the SiCl$_4$-treatment of the mordenite salt may be preferably effected at a temperature ranging from about 50° to about 900° C., in particular from about 300° to about 800° C., under a SiCl$_4$ partial pressure ranging from 0.01 to 1000 kPa, in particular from 1 to 100 kPa.

The ion exchange of the mordenite in the present invention may be preferably effected by a treatment with an ammonium salt such as ammonium nitrate, but any other known methods such as a treatment with acids so long as it is conducted under such conditions that will not cause dealumination of the mordenite.

The reaction for the synthesis of methylamines with the use of the catalyst of the present invention may be preferably effected at a temperature ranging from about 200° to about 500° C., in particular from about 250° to about 400° C., under a pressure ranging from 1 to 1000 kPa, in particular from 2 to 600 kPa, and at a nitrogen to carbon molar ratio (N/C) ranging from 0.1 to 10, in particular from 1 to 5.

The foregoing Test Examples and Examples are given to further illustrate the present invention. Unless otherwise indicated, all parts, percents, ratios and the like are by weight.

TEST EXAMPLE 1

(1) Method

Figure 2:
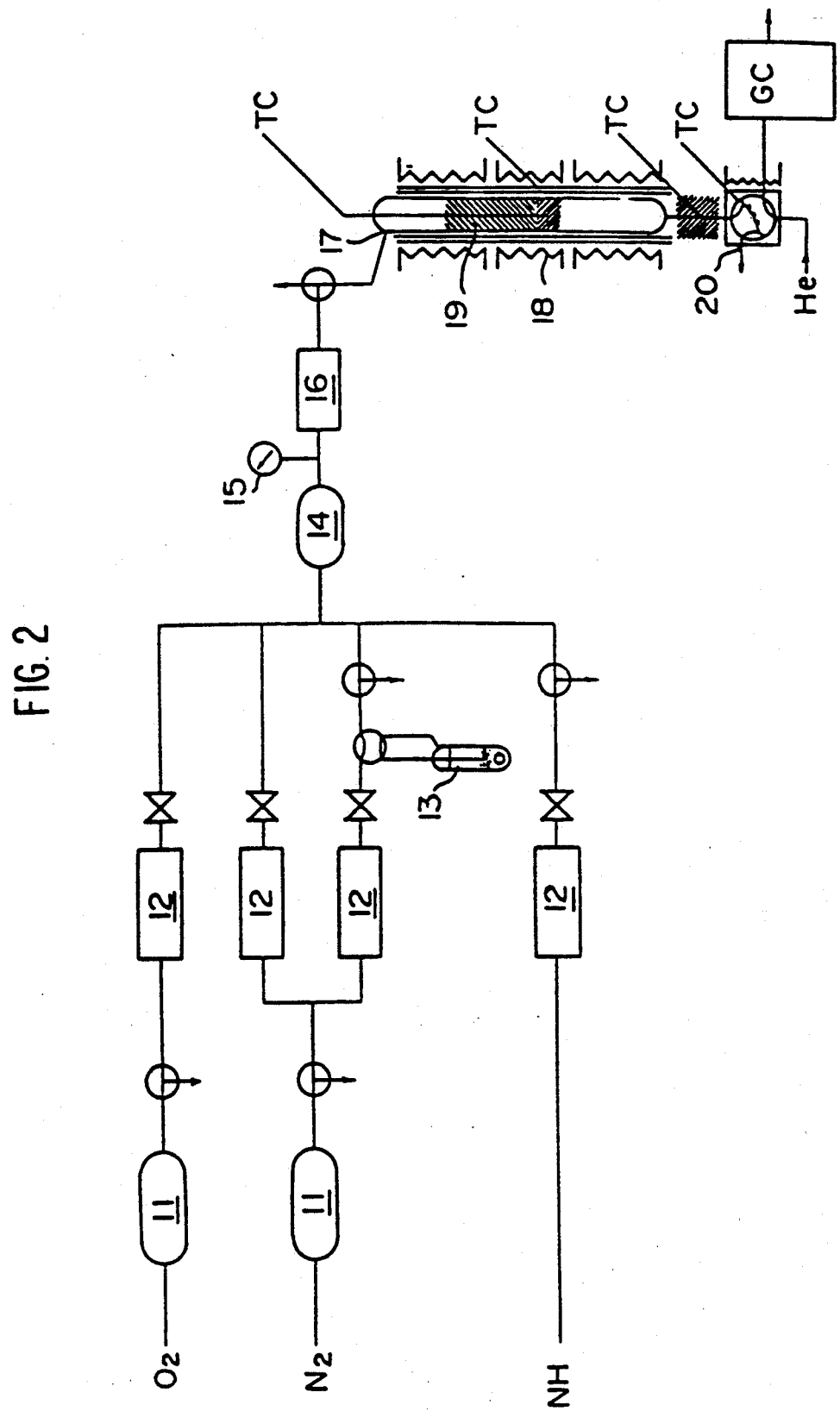
FIG. 2 shows an atmospheric pressure flow-through type reaction device for the same.

By using an atmospheric pressure flow-through type reaction device as shown in FIG. 2 and Examples in detail, methylamines were synthesized under a N$_2$ gas stream at a ratio of starting ammonia and methanol (NH$_3$/CH$_3$OH) of 1 by mol. The reaction temperature was 573° to 723° K. Gas chromatography (GC) was employed as an analytical means. After conducting the treatment with silicon tetrachloride in an atmospheric pressure flow-through system at 973° K. for 2 hours under a N$_2$ gas stream, ion exchange was effected so as to convert the treated product into an H-type. The adsorption of pyridine and ammonia was tested by means of IR in order to examine the pore size of the catalyst.

(2) Result

Table 1 shows the rates of conversion of MeOH and the rates of methylamine selection at the reaction temperature of 653° K. achieved by using various H-type zeolites as a catalyst. The rate of methylamine selection is expressed by referring the sum of methylamines as to 100%, while the rate of selection of dimethyl ether (DME) formed as a by-product is expressed based on the total products.

TABLE 1

| Catalyst | CONV. (%) | DME (%) | MMA (%) | DMA (%) | TMA (%) |
|---|---|---|---|---|---|
| Control | | | | | |
| Silica/alumina (SAL-2) | 93.2 | 27.1 | 24.4 | 14.6 | 61.0 |
| H-zeolite Y (H-Y 5,6) | 99 | 10.6 | 15.4 | 25.6 | 59.0 |
| H-mordenite Si/Al 10 (H-M 10) | 94.1 | 7.6 | 31.4 | 31.0 | 37.6 |
| H-mordenite Si/Al 15 (H-M 15) | 88.4 | 16.4 | 27.3 | 29.4 | 43.3 |
| H-mordenite Si/ | 86.4 | 20.6 | 26.6 | 25.8 | 47.6 |

TABLE 1-continued

| Catalyst | CONV. (%) | DME (%) | MMA (%) | DMA (%) | TMA (%) |
|---|---|---|---|---|---|
| A120 (H-M 20) Invention | | | | | |
| (H)M/SiCl4(Si/ A110) (H-SC-M 10) Control | 98.9 | 0.8 | 35.8 | 61.7 | 2.5 |
| Zeolite H-ZSM5-25 | 74.0 | 12.0 | 22.0 | 28.0 | 50.0 |
| Thermodynamic equilibrium value | | | 11.4 | 23.0 | 65.6 |

[Note]
DME: Dimethyl ether.
MMA: Monomethylamine.
DMA: Dimethylamine.
TMA: Trimethylamine.

Zeolite Y had superior activity to conventional amorphous silica alumina. However, the rate of selection of TMA thereof of zeolite Y was equal to the thermodynamic equilibrium value thereof, which suggests that it might be unsuitable as a catalyst. The H type ZSM5 showed a low reaction activity and a scarcely improved rate of selection. On the other hand, the H-mordenite showed a reaction activity almost the same as that of silica alumina and high selectivity for DMA and MMA. It was found that the reaction activity of the H-mordenite and the selectivity for DMA and MMA thereof increased with a decrease in the Si/Al ratio thereof, namely, with an increase in the amount of the acid. When Na-mordenite was treated with silicon tetrachloride and converted into H-type by ion exchange, the reaction activity was further improved and the selectivity for DMA and MMA were also extremely elevated. Furthermore, the formation of DME was considerably suppressed in this case.

TEST EXAMPLE 2

(1) Method

The catalyst employed was obtained by treating mordenite with silicon tetrachloride at 973° K. for 2 hours under a $N_2$ gas stream followed by ion-exchanging into an H-type. The synthesis of methylamines was effected using an atmospheric pressure flow-through type device of FIG. 2 at a $NH_3$/MeOH ratio of 1.0 (by mol), at 573° to 723° K. under a $P_{MeOH}$ of 2.8 kPa and under a $N_2$ gas stream. GC was employed as an analytical means. The adsorption of methylamines was tested to thereby evaluate the change in pore size caused by the silicon tetrachloride treatment. Further, characterization was conducted by IR and NMR.

(2) Result

TABLE 2

| Catalyst | DME (%) | MMA (%) | DMA (%) | TMA (%) |
|---|---|---|---|---|
| Control | | | | |
| Al2O3 | 43 | 16 | 13 | 28 |
| SiO2/Al2O3 | 27 | 18 | 10 | 45 |
| H-Y | 10 | 13 | 23 | 54 |
| H-M | 7 | 29 | 28 | 36 |
| Invention | | | | |
| H-SC-M | 1 | 36 | 62 | 2 |
| Control | | | | |
| H-ZSM5 | 11 | 24 | 28 | 37 |

First, various solid acid catalysts were examined. As a result, H—Y and H—M zeolites having Bronsted acid sites showed high activities. In the case of H-mordenite, the activity increased with a decrease in the Si/Al ratio. On the other hand, H-ZSM5 having a high Si/Al ratio showed a low activity. A catalyst (H—SC—M) obtained by treating mordenite with silicon tetrachloride followed by conversion into an H-type showed an activity comparable to that of H—M. Table 2 shows the selection rates of products of solid acid catalysts at a reaction temperature of 653° K. In the cases of alumina and silica/alumina, DME was formed at higher rates, which might be caused by weak acid centers on the surface of these catalysts. In the cases of H—Y, H—M and H-ZSM5, the amount of the formed DME corresponded almost to half of that in the case of the silica/alumina, while the selectivity for DMA was approximately 30%. On the other hand, little DME was formed in the case of H—SC—M. In this case, the formation of TMA was well suppressed as well (approximately 2.0%) while the selectivity for DMA and MMA showed a remarkable increase up to 97%.

In order to determine the reason for the suppression of the formation of TMA, an adsorption test on methylamines was carried out. Table 3 shows the results. In the case of H—M, a large amount of TMA was adsorbed. In the case of H—SC—M, the amount of adsorbed TMA was small (0.42) and the amount of adsorbed DMA showed little decrease compared with the case of H—M. Na—M showed little adsorption, in general, which was caused by the fact that this catalyst had no Bronsted acid centers. These facts demonstrate that the pore size of H—SC—M was effectively controlled by the treatment with silicon tetrachloride so as to give a high DMA selectivity. Pyridine, having a molecular size almost the same as that of TMA, was adsorbed and then analyzed by IR. In the case of H—M, pyridine was incorporated within pores and a peak based on Bronsted acid was observed. On the other hand, pyridine was scarcely adsorbed by H—SC—M. Next, ammonium, having a smaller molecular size, was adsorbed by these catalysts. As a result, ammonia was incorporated within pores of both of these catalysts and thus peaks based on Bronsted acid centers were observed. These facts suggest that the treatment with silicon tetrachloride would make it possible to control the pore size and acid centers on the surface of the catalyst while sustaining the acidic characteristics within the pores.

TABLE 3

| Zeolite | Si/Al | Adsorption Amount | | |
|---|---|---|---|---|
| | | MMA | DMA | TMA |
| Control | | | | |
| H-M | 9.9 | 2.90 | 2.71 | 1.27 |
| Na-M | 9.8 | 1.59 | 1.47 | 0.75 |
| Invention | | | | |
| H-SC-M | 10.9 | 1.84 | 2.04 | 0.42 |
| Control | | | | |
| SC-Na-M | 10.7 | 1.40 | 0.83 | 0.50 |

[Note]:
Each zeolite was treated with methylamine under a kPa of 1.3 at 373° K.

EXAMPLE

(1) Preparation of Catalyst

(1)-1 SiCl4 Treatment

An atmospheric pressure flow-through type reaction device as in FIG. 1 was employed. The flow rate of $N_2$ gas was controlled with the use of a line for the synthesis of methylamines. Since silicon tetrachloride is highly corrosive, exclusive pipes were employed therefor. Approximately 3 g of a sample was molded into a tablet, ground and then filled in reaction tube 7 made of quartz glass. α-Alumina was packed below catalyst layer 9 so as to locate the catalyst at a part of oven 8 of uniform temperature distribution. The temperature was increased up to 973° K. at a rate of 10° K./min while feeding $N_2$ gas at a rate of 150 ml/min. After maintaining the temperature at 973° K. for 30 minutes, $N_2$ gas, which had been passed through a $SiCl_4$ bubbler in an ice-bath at 273° K. was fed at 150 ml/min for 2 hours under atmospheric pressure. Liquid nitrogen trap 10 was provided below the reaction tube so as to trap silicon tetrachloride. After maintaining such for 1 hour under an $N_2$ purge at 150 m ml/min, the reaction mixture was cooled. The catalyst thus treated was boiled in distilled water for 30 minutes. Next, it was washed with distilled water until no chloride ion was further detected with the use of a centrifuge. Then, it was calcined by heating to 723° K. in an oven at a rate of 2.5° K./min and then maintaining this temperature for 2 hours. The trapped silicon tetrachloride was poured into an evaporating dish in a draft chamber and water was added thereto. When the generation of heat ended, it was neutralized with sodium carbonate and the gel thus formed was filtered with suction.

(1)-2 Ion Exchange 2.0 g of a sample was introduced into a short-neck flask (200 $cm^3$) and a 100 $cm^{-3}$ of a 1.0 $mol/cm^3$ aqueous solution of $NH_4NO_3$ was added thereto. A cooling tube was provided at the upper part of the flask. Then, the mixture was maintained at 333° K. in a thermostat for 4 days. The $NH_4NO_3$ solution was exchanged daily with the use of a centrifuge. The $NH_4$-type zeolite thus obtained was thoroughly washed with distilled water and calcined for 2 hours by heating to 723° K. in an oven at a rate of 2.5° K./min.

(2) Synthesis of Methylamines (2)-1 Reaction

An atmospheric pressure flow-through type reaction device as in FIG. 2 was employed. Each catalyst as specified in Table 4 below was molded into a tablet, ground and introduced into quartz glass reaction tube 17. Powdery quartz was packed above and below the catalyst layer. A thermocouple was inserted at the center of the catalyst layer in order to monitor the temperature of the catalyst in such a manner not to exceed the definite temperature due to the heat of reaction. The feed of each material gas was controlled with the use of a thermal mass flow controller 12 (manufactured by Kojima Seisakusho). Flow controllers of full-scale of 3, 200, 500 and 200 $cm^3$/min were employed for $NH_3$, $N_2$ (bubbler), $N_2$ (bypass) and $O_2$ (calcining), respectively. First, a flow controller of 500 $cm^3$/min was selected for $NH_3$. However, it was impossible to control minor flow thereby. Thus, it was substituted with a flow controller of 3 $cm^3$/min.

The system was heated to 723° K. at 2.5° K./min while flowing $N_2$ at 50 ml/min and then maintained at the temperature for 1 hour. Next, the reaction temperature was decreased to 573°-673° K. and methanol and ammonia were fed at a molar rate of 1/1 so as to initiate the reaction. The relationship between the weight of the catalyst W (g) and the amount of the fed methanol F (mol/hr) was represented by the formula: W/F=62 g·hr/mol. The methanol was saturated by feeding $N_2$ gas into a cooled MeOH bubbler prior to the introduction of the reaction tube. The outlet of the reaction tube and a sampling cock were heated to 303° K. to thereby inhibit closing of the pass way or aggregation of reaction products. A sampling valve was driven with $N_2$ gas (4 $kgW/cm^2$). In order to achieve an exact retention time, the on-off of the sampling valve was synchronized with an integrator by controlling the relay of GC.

TABLE 4

| Catalyst | Conversion of MeOH (%) | Catalyst Activity (conversion of MeOH into methylamine) (%) | Selectivity (%)*1 | |
|---|---|---|---|---|
| | | | DMA | TMA |
| NaM (Control) | 14.5 | 4.6 | —*2 | — |
| HM (Comparison) | 94.1 | 86.9 | 28.6 | 37.7 |
| NaM/$SiCl_4$ (Comparison) | 13.8 | 5.0 | — | — |
| (H)M/$SiCl_4$ (Invention) | 98.9 | 98.1 | 61.2 | 2.5 |
| HM/$SiCl_4$ (Comparison) | 84.3 | 29.3 | — | — |

[Note]
*1 Definition of selectivity: Ratio (%) of each methylamine as carbon atoms based on the Formed MMA + DMA + TMA + DME.
DMA Selectivity =

$$\frac{2 \times DMA \text{ \% by mol}}{2 \times DME \text{ \% by mol} + MMA \text{ \% by mol} + 2 \times DMA \text{ \% by mol} + 3 \times TMA \text{ \% by mol}} \times 100$$

*2 "—" means that the catalytic activity showing the conversion of MeOH into methylamine is such a low value that the catalyst is unsuitable and thus no selectivity is given.

Now the fact that removal of aluminum from the catalyst of the present invention used in the Example does not occur is illustrated by reference to FIG. 3.

FIG. 3 shows the results of NMR analysis of NaM, HM, NaM/$SiCl_4$, HM/$SiCl_4$ and (H)M/$SiCl_4$. NaM and HM, which were not treated with $SiCl_4$, showed no removal of aluminum. On the other hand, HM/$SiCl_4$ obtained by treating HM with $SiCl_4$ showed substantial removal of aluminum, as shown by a peak Al(Oct). In contrast thereto, (H)M/$SiCl_4$ of the present invention showed little removal of aluminum.

FIG. 4 shows the results of IR analysis. Peaks corresponding to wavelengths of 3603 to 3610 $cm^{-1}$ show solid acid centers. When HM was treated with $SiCl_4$, most of the acid centers of HM showing high peaks disappeared. In contrast thereto, quite high peaks were observed in the case of (H)M/$SiCl_4$ of the present invention. It is further shown that HM adsorbed both of ammonia and pyridine, which suggests that the use of HM as a catalyst might scarcely suppress the formation of trimethylamine, since the molecular size of pyridine is almost the same as that of trimethylamine. In contrast thereto, (H)M/$SiCl_4$ of the present invention scarcely adsorbed pyridine, which demonstrates that this catalyst can suppress the formation of trimethylamine.

The process of the present invention, which comprises selecting a specific mordenite starting material, treating the material with $SiCl_4$ and then effecting ion exchange, makes it possible to produce a modified H-mordenite having substantially narrowed and uniform pores, compared with conventional H-mordenite, without any aluminum removal occurring.

Such a mordenite, which has a number of solid acid sites and extremely fine pores of a uniform pore size, has a surprising selectivity when employed as a catalyst.

While the invention has been described in detail and with reference to specific embodiments thereof, it will be apparent to one skilled in the art that various changes and modifications can be made therein without departing from the spirit and scope thereof.

What is claimed is:

1. A process for the synthesis of methylamines comprising reacting methanol and ammonia in the presence of a catalyst comprising a modified H-mordenite obtained by a process which comprises bringing an alkali metal or alkaline earth metal mordenite into contact with SiCl$_4$ with heating and then converting the treated mordenite into an H-mordenite via ion exchange.

2. The process of claim 1, wherein the catalyst is produced without significant dealumination.

* * * * *